United States Patent [19]

Adachi et al.

[11] Patent Number: 4,681,771
[45] Date of Patent: Jul. 21, 1987

[54] SWEETENER

[75] Inventors: Takashi Adachi, Kanagawa; Hidemasa Hidaka, Saitama, both of Japan

[73] Assignee: Meiji Seika Kaisha Ltd., Tokyo, Japan

[21] Appl. No.: 787,026

[22] Filed: Oct. 15, 1985

Related U.S. Application Data

[63] Continuation of Ser. No. 413,097, Aug. 30, 1982, abandoned, which is a continuation-in-part of Ser. No. 249,585, Mar. 31, 1981, abandoned.

[30] Foreign Application Priority Data

Mar. 31, 1980 [JP] Japan .................................. 55-40193
Jun. 24, 1980 [JP] Japan .................................. 55-84547
Dec. 12, 1980 [JP] Japan ................................. 55-174667

[51] Int. Cl.$^4$ .............................................. A23G 3/00
[52] U.S. Cl. .................................... 426/658; 426/804; 127/29
[58] Field of Search ....................... 426/658, 804, 558; 127/29, 30; 536/1.1, 119, 123, 126; 435/97, 74, 72

[56] References Cited

U.S. PATENT DOCUMENTS

| | | | |
|---|---|---|---|
| 3,703,440 | 11/1972 | Okada | 127/29 |
| 3,931,398 | 1/1976 | Gaffar | 424/92 |
| 4,133,875 | 1/1979 | Hillman | 435/172.1 X |
| 4,276,379 | 6/1981 | Heady | 435/97 |

FOREIGN PATENT DOCUMENTS

| | | | |
|---|---|---|---|
| 1336002 | 11/1973 | United Kingdom . | |
| 1352633 | 5/1974 | United Kingdom . | |
| 2072679 | 10/1981 | United Kingdom | 435/72 |

OTHER PUBLICATIONS

Webster's New Collegiate Dictionary, G. & C. Merrians Co., 1960, p. 322.

Primary Examiner—Kenneth M. Schor
Attorney, Agent, or Firm—Sughrue, Mion, Zinn, Macpeak, and Seas

[57] ABSTRACT

A low-calorific and low-cariogenic sweetener, and processes for the preparation and use thereof, are described, said sweetener comprising oligosaccharides having from 1 to 4 molecules of fructose bound to sucrose.

2 Claims, No Drawings

SWEETENER

CROSS REFERENCE OF THE RELATED APPLICATION

This is a continuation of application Ser. No. 413,097 filed 8-30-82 now abandoned, which is a continuation-in-part of application Ser. No. 249,585 filed 3-31-81 now abandoned.

FIELD OF THE INVENTION

This invention relates to a low-calorific and low-cariogenic sweetener (that is, a sweetening agent having little or no tendency for causing tooth decay), comprising oligosaccharides, obtained by reacting fructosyl transferase with sucrose, and having from 1 to 4 molecules of fructose bound to sucrose, and relates to processes for preparing and using the sweetener.

BACKGROUND OF THE INVENTION

Sucrose has heretofore been widely used in confectionary and foods due to its excellent sweetness, body taste, crystallinity, etc. However, sucrose can form a substrate for dextran sucrase produced by intraoral microorganisms, and, as a result, frequent intake of sucrose leads to formation of insoluble dextran in the mouth; thus formation of dental plaque is accelerated. Therefore, sucrose is said to possess cariogenicity.

The mechanism of the occurrence of dental caries appears to comprise the following steps: (1) a step wherein sucrose is converted to insoluble dextran by the action of dextran sucrase produced by a cariogenic microorganism of *Streptococcus mutans* or the like, and, at the same time, adsorbs the cariogenic microorganisms to form dental plaque; and (2) a step wherein fermentable sugars such as glucose and sucrose are fermented by the microorganisms in the dental plaque deposited on the surface of the teeth to produce organic acids (comprising mainly lactic acid) which reduce pH and cause a deliming phenomenon.

Polyols such as xylytol and saccharin and synthetic sweeteners such as cyclamate and aspartame are known as low-cariogenic sweeteners. But, these sweeteners have defects that, for example, the former easily causes diarrhea and the latter lacks body taste.

Furthermore, a low-calorific sweetener is desired for a diet food.

It is, therefore desired to develop a low-calorific and low-cariogenic sweetener having the excellent properties of sucrose and not having the above defects.

SUMMARY OF THE INVENTION

In view of the cariogenicity and high calorie of sucrose, it is an object of the present invention to provide a sweetener having the desirable properties of sucrose, but having low cariogenicity and low calorie.

Thus according to the present invention, a low-calorific and low-cariogenic sweetener is provided comprising oligosaccharides having from 1 to 4 molecules of fructose bound to sucrose.

The invention also comprises a process for preparing the low-calorific and low-cariogenic sweetener, comprising reacting sucrose in the presence of fructosyl transferase.

The invention also comprises a process for preparing low-calorific and low-cariogenic food products (including both solid foods and beverages), and more particularly to a process for preparing low-calorific and low-cariogenic food products using the novel sweetener of this invention.

The invention further comprises a process for preparing a low-calorific and low-cariogenic sweetener containing sorbitol and mannitol by selectively catalytically reducing glucose and fructose contained as by-products in an oligosaccharide composition which is obtained by reacting sucrose in the presence of fructosyl transferase and which contains sugars of oligosaccharides having from 1 to 4 molecules of fructose bound to sucrose, unreacted sucrose, and glucose and fructose.

DETAILED DESCRIPTION OF THE INVENTION

This invention has resulted from extensive investigations to develop a low-calorific and low-cariogenic sucrose-related material still having the excellent properties of sucrose, by which it has now been discovered that oligosaccharides obtained by reacting sucrose in the presence of fructosyl transferase, and particularly oligosaccharides such as that in which one molecule of fructose is bound to sucrose (hereinafter referred to as $GF_2$), that in which two molecules of fructose are bound to sucrose (hereinafter referred to as $GF_3$), that in which three molecules of fructose are bound to sucrose (hereinafter referred to as $GF_4$), that in which four molecules of fructose are bound to sucrose (hereinafter referred to as $GF_5$), are low-calorific and also exhibit substantially no effects of dextran sucrase produced by intraoral microorganisms (such as *Streptococcus mutans*) and decrease the formation of insoluble dextran from sucrose which is to be caused by dextran sucrase. The oligosaccharides of $GF_2$, $GF_3$, $GF_4$, $GF_5$ according to this invention can be isolated and purified, by means of, for example, carbon chromatography (e.g., chromatography using activated powdered charcoal), ion-exchange chromatography, or the like, from the sugar mixture obtained by reacting fructosyl transferase with sucrose. From a practical point of view, however, the oligosaccharide mixture is preferably used per se. The sugar mixture also typically contains some unreacted sucrose, oligosaccharides of $GF_2$, $GF_3$, etc., produced by the transfer reaction, and the by-products of glucose and fructose, produced as by-products of the reaction.

However, this sugar mixture also exhibits the effects of dextran sucrase produced by intraoral microorganisms, but due to the presence of the oligosaccharides the insoluble dextran is produced in a less quantity. This is attributed to the fact that the oligosaccharides of $GF_2$, $GF_3$, etc., depress formation of insoluble dextrans from sucrose in spite of the presence of sucrose, and that insoluble dextran is not produced from the oligosaccharides of $GF_2$, $GF_3$, etc.

Thus, a mixture or composition containing oligosaccharides having from 1 to 4 molecules of fructose bound to sucrose produces less insoluble dextran, which is believed to be a main cause of dental caries, and the oligosaccharides of $GF_2$, $GF_3$, etc., depress formation of dextran from sucrose.

Further, the composition of the present invention possesses excellent properties as a sweetener, such as good sweetness, proper body taste, good moisture retention, etc., in addition to exhibiting low cariogenicity and low calorie.

More particularly, the composition shows a sweetness of 60 to 80, taking the sweetness of sucrose as 100, and has specific flavor. Sweetness is evaluated by Threshold method described in *Sweeteners and Dental Caries*, written by J. H. Shaw, page 45, Information Retrieval Incorporation. Also, $GF_2$, $GF_3$, etc., are difficultly colored upon processing because they are non-reducing sugars. Furthermore, this sweetener shows about the same viscosity and osmotic pressure as sucrose, and is non-crystalline. Therefore, when mixed with sucrose, fruit sugar, lactose or the like, it can inhibit crystallization. This property is thought to be advantageous in practical use. Still further, this sweetener has about the same freezing point depression as sucrose, and has excellent moisture retention properties.

As is described above, this sweetener has various properties required for conventional sweeteners, and, therefore, it can be used in any food product in place of the conventionally used sweeteners such as sugar, acid-saccharified wheat gluten (mizuame), isomerized sugar, etc., and the food product thereby obtained will be less cariogenic and less calorific than a food product obtained using the conventional sweeteners.

As is described above, the composition containing oligosaccharides having from 1 to 4 molecules of fructose bound to sucrose (hereinafter referred to as a low-cariogenic sweetener) is a less dental cariogenic and less calorific sweetener composition. The inventors have also intensively investigated the process for the industrial production of this low cariogenic and low calorific sweetener and have completed a second invention. That is, the sweetener can be obtained by reacting sucrose in the presence of fructosyl transferase.

The fructosyl transferase acts mainly on the sucrose to serve the $\beta$-1,2 bond between fructose and glucose, and transfers the resulting fructose to sucrose to yield $GF_2$, and further transfer fructose to $GF_2$ to yield $GF_3$. It is different from inulosucrase [2.4.1.9] and levansucrase [2.4.1.10] described in *Enzyme Nomenclature* (Academic Press, 1978) in that the reaction products are oligosaccharides wherein fructose is bound to sucrose, as $GF_2$, $GF_3$, etc.

As a source for the enzyme, there are microorganisms such as fungi [e.g., genus Aspergillus (*Aspergillus niger* ACE-2-1, ATCC 20611, etc.), genus Penicillium (*Penicillium nigricans*, etc.), genus Fusarium (*Fusarium lini* IAM 5008, etc.), genus Gloeosporium (*Gloeosporium kaki* IAM 5011, etc.), etc.] and yeasts [e.g., genus Saccharomyces (*Saccharomyces cerevisiae*, etc.), genus Rhodotorulla (*Rhodotorulla glutinis*, etc.), genus Pichia (*Pichia miso*, etc.), genus Hansenula (*Hansenula miso*, etc.), genus Candida (*Candida tropicalis*, etc.), *Aureobasidium pullulans* var. melanigenum A-8, ATCC 20612] and vegetable-produced enzyme such as from Asparagus officinalis, Helianthus tuberosus L., etc. Fructosyl transferase of microorganism origin can be obtained by cultivating the microorganism at an optimal temperature for the microorganism, i.e., 25° C. to 30° C., for from 24 to 96 hours using a known appropriate medium, for example, a medium containing 5.0% sucrose, 1.0% peptone, 0.7% meat extract, and 0.3% NaCl and, after completion of cultivation, removing cells of the microorganism by filtration or centifugation to obtain a culture filtrate. The filtrate itself or enzyme obtained by purifying the filtrate according to a conventional process known for the purification of enzyme, such as ultrafiltration, salting out (that it, salt and other impurities are removed therefrom) with sodium sulfate, solvent precipitation, gel filtration or ion-exchange chromatography can be used.

Enzyme of vegetable origin can be obtained by destroying vegetable tissue through physical means such as grinding, and extracting the enzyme. The crude extract itself, or enzyme obtained by purifying the extract in a conventional manner (such as ethanol precipitation, $(NH_4)_2SO_4$ salting out, etc.) can be used.

The low-calorific and low-cariogenic sweetener can then be obtained by reacting sucrose in the presence of the thus-obtained enzyme. As a result of various investigations as to suitable reaction conditions, the following conditions have been found to be preferable. Particularly, sucrose concentration upon the transfer reaction is generally adjusted to from 5% to 70%, and preferably from 30% to 60% by weight. Reaction pH and reaction temperature are generally from 4.0 to 7.0 and from 25° C. to 65° C., and preferably 50° C. to 60° C., respectively, although depending upon the enzyme origin the most preferably conditions may vary. As to the enzyme quantity, from 5 to 200 units, and preferably from 20 to 80 units, of enzyme is used per g of sucrose. The enzyme quantity is herein indicated in terms of "units" taking, as one unit an enzyme quantity having the activity of yielding 1 $\mu$mol of glucose per 2.5 ml of a reaction solution when the reaction is conducted by adding 0.5 ml of an enzyme solution to 1.0 ml of a 5% sucrose solution and 1.0 ml of a buffer solution of 5.0 in pH followed by reacting at 40° C. for 60 minutes.

After completion of the transfer reaction, the reaction mixture is heated to 100° C. to deactivate the enzyme, decolorized with active carbon, desalted with an ion-exchange resin, and concentrated to obtain the end product. Analysis of the transfer reaction composition can be conducted, for example, by high speed liquid chromatography using Microbondapack CH column (made by Waters Associates Incorporation) and a solvent of acetonitrile/water (80/20 by volume).

The thus-obtained low-calorific and low-cariogenic sweetener has a composition consisting of, for a typical example, 28% by weight glucose, 2% fructose, 11% sucrose, 28% $GF_2$, 25% $GF_3$, 5% $GF_4$, and 1% $GF_5$. This constituent sugar composition greatly varies depending upon the reaction conditions.

As $GF_2$ of the oligosaccharides, there are illustrated O-$\beta$-D-fructofuranosyl-(2→1)-O-$\beta$-fructofuranosyl-(2→1)-$\alpha$-D-glucopyranoside, O-$\beta$-D-fructofuranosyl-(2→6)-O-$\beta$-D-glucopyranosyl-(1→2)-$\beta$-D-fructofuranoside, O-$\beta$-D-fructofuranosyl-(2→6)-O-$\beta$-fructofuranosyl-(2→1)-$\alpha$-D-glucopyranoside, etc. As $GF_3$, there are illustrated O-$\beta$-D-fructofuranosyl-(2→[1-O-$\beta$-D-fructofuranosyl-2]$_2$→1)-$\alpha$-D-glucopyranoside, O-$\beta$-D-fructofuranosyl-(2→6)-O-[$\beta$-D-fructofuranosyl-(2→2)]-O-$\alpha$-D-glucopyranosyl-(1→2)-$\beta$-D-fructofuranoside, etc., and, as $GF_4$, there are illustrated O-$\beta$-D-fructofuranosyl-(2→[1-O-$\beta$-D-fructofuranosyl-2]$_3$→1)-$\alpha$-D-glucopyranoside, etc. As $GF_5$, there are illustrated O-$\beta$-D-fructofuranosyl-(2→[1-O-$\beta$-D-fructofuranosyl-2]$_4$→1)-$\alpha$-D-glucopyranoside, etc.

The effects of the sweetener of the present invention and effects of individual ingredients of $GF_2$, $GF_3$, $GF_4$, and $GF_5$ will be described in more detail by experimental examples described below.

Table 1 in Test Example 1 to be described hereinafter shows the amounts of insoluble dextrin onbtained from $GF_2$, $GF_3$, $GF_4$, and $GF_5$ using dextran sucrase obtained by cultivating *Streptococcus mutans*, ATC 25175 strain, in comparison with the result as to sucrose. As is clear from the table, insoluble dextran is not obtained from $GF_2$, $GF_3$, $GF_4$, and $GF_5$.

Results of examining whether $GF_2$ and $GF_3$ depress or do not depress production of insoluble dextran from sucrose by dextran sucrase are tabulated in Table 2 in Text Example 2 to be described hereinafter. As is clear from the Table 2, $GF_2$ and $GF_3$ are found to depress production of insoluble dextran from sucrose.

Table 4 in Test Example 3 to be described hereinafter shows the amount of insoluble dextran obtained from the sweetener composition prepared under different conditions and therefore having different composition in comparison with the result as to sucrose. As is clear from the table, the transfer compositions yielded the insoluble dextran in lower amounts than sucrose. In particular, where the content by weight of the sum of oligosaccharides of $GF_2$, $GF_3$, $GF_4$, etc., is two times as much as, or more than that of, the content of free sucrose in the sweetener composition is preferred. That is, where ratio of the content by weight of the sum of oligosaccharides to the free sucrose content by weight at least 2.0/1, the amount of insoluble dextran produced is 50% or less than that produced using sucrose; thus such compositions are particularly preferable.

As is described above, a mixture or composition containing the oligosaccharides having from 1 to 4 molecules of fructose bound to sucrose produces less insoluble dextran which is a main cause of dental caries, and the oligosaccharides of $GF_2$, $GF_3$, etc., depress formation of dextran from sucrose.

Such a sugar composition does not exhibit the effects of dextran sucrase yielded by S*Streptococcus mutans*, etc., and hence insoluble dextran is not produced when the sugar composition is intaken and, in this sense, the composition is less cariogenic. However, though oligosaccharides of $GF_2$, $GF_3$, etc., in the composition are not substantially fermented by the microorganisms of *Streptococcus mutans*, etc., thus producing only slight amounts of organic acids therefrom, unreacted sucrose and glucose and fructose produced as by-products in the transfer reaction can be converted to organic acids. Thus, the sugar composition yields a less amount of organic acid as compared to sucrose, but is still not completely satisfactory.

As a result of intensive investigations on this particular point, it has also been discovered that glucose and fructose exist only in a small amount in the composition and can be selectively converted to sorbitol and mannitol by catalytic reduction of the sugar composition, which has been obtained by reacting sucrose in the presence of fructosyl transferase, under specific conditions, and that the amount of lactic acid produced from the thus-obtained sweetener composition by the action of microorganism is only about 20% of that produced by sucrose. (See Test Example 4.) That is, this invention also provides a process for preparing novel sweetener containing sorbitol and mannitol, which comprises reacting sucrose in the presence of fructosyl transferase, to obtain a sugar solution containing glucose, fructose, sucrose, and oligosaccharides having 1 to 4 molecules of fructose bound to sucrose, and subjecting this sugar solution to catalytic reduction while maintaining the pH of the solution at from 7 to 9.

More particularly, it has been found that glucose and fructose are selectively reduced to yield sorbitol from glucose and sorbitol and mannitol from fructose without decomposing the oligosaccharides of $GF_2$, $GF_3$, $GF_4$, etc., by adding, for example, disodium hydrogenphosphate to the aqueous solution of abovedescribed sugar composition to adjust the pH of the aqueous solution to from 7 to 9, and stirring the mixture in the presence of 3 to 10%, based on solids, of a nickel catalyst (Raney nickel, nickel formate, nickel-on-diatomaceous earth, etc.) to conduct the reduction reaction at 50° to 130° C. under a reacting hydrogen pressure of 50 to 120 $kg/cm^2$. Of the reaction conditions, adjustment of pH is particularly important. When the catalytic reduction is conducted, for example, at a pH of 6 or less, the oligosaccharides of $GF_2$, $GF_3$, $GF_4$, etc., are decomposed to yield sorbitol and mannitol in large amounts, and thus selective reduction of glucose and fructose is preferably conducted at a pH of from 7 to 9.

The thus-obtained sweetener composition contains, typically, about 37% sorbitol, 2% mannitol, 10% sucrose, 22% $GF_2$, 22% $GF_3$, and 7% $GF_4$. As is shown in Test Example 4, it has been demonstrated that the amount of lactic acid produced from the composition by the action of *Streptococcus mutans* is much less than that from sucrose or from the sugar composition obtained by acting fructosyl transferase on sucrose.

As is described above, the sweetener composition of the present invention containing sorbitol, mannitol, oligosaccharides of $GF_2$, $GF_3$, $GF_4$, etc., and a slight amount of sucrose is a poor substrate for dextran sucrose yielded by *Streptococcus mutans*, and hence it allows production of insoluble dextran in only slight amounts. In addition, less susceptibility of the composition to fermentation by *Streptococcus mutans* reduces the amount of cariogenic lactic acid to be produced.

Accordingly, the composition is a sweetener showing strong anti-cariogenic properties.

TEST EXAMPLE 1

*Streptococcus mutans* ATCC 25175 strain was cultivated under anaerobic conditions using a medium containing glucose and triptocase and, after separating cells of the microorganisms, the filtrate was concentrated and purified by ultrafiltration to prepare dextran sucrase.

Then, 1.0 ml of a 1% sugar solution, 1.5 ml of a 0.67M phosphate buffer solution (pH 7.0), and 0.25 ml of the above-described enzyme solution were mixed and reacted for 4 hours at 37° C. Water-insoluble dextran thus-prepared was precipitated by centrifugation at 3,000 rpm to collect the precipitate. The precipitate was washed twice each with 5 ml of 70% ethanol, dissolved in 2.5 ml of a 1M potassium hydroxide solution, and subjected to a phenol-sulfuric acid method to determine the quantity of yielded dextran. Additionally, as the sugar solutions, 1% solutions of $GF_2$, $GF_3$, $GF_4$, and $GF_5$ were used respectively. As $GF_2$, $GF_3$, $GF_4$, and $GF_5$, fractions purified by subjecting a sugar composition (obtained by reacting sucrose in the presence of fructosyl transferase) to carbon chromatography (using activated powdered charcoal) to provide a single spot in thin layer chromatography were used. Results thus-obtained obtained are shown in Table 1.

TABLE 1

| Sample | Dextran Yielded in the Reaction Solution ($\gamma$) |
| --- | --- |
| Sucrose | 740 |
| $GF_2$ | 0 |
| $GF_3$ | 0 |
| $GF_4$ | 0 |
| $GF_5$ | 0 |

As is shown in Table 1, no dextran was yielded from $GF_2$, $GF_3$, $GF_4$, and $GF_5$.

TEST EXAMPLE 2

In this example, it was examined whether $GF_2$ and $GF_3$ depress or do not depress production of insoluble dextran from sucrose when sucrose is exposed to dextran sucrose prepared in Test Example 1 in the presence of $GF_2$ and $GF_3$. Additionally, reaction conditions were as follows: 1.0 ml of each sugar solution (containing the sugar given in Table 2), 1.5 ml of a 0.67M phosphate buffer solution (pH 7.0), and 0.25 ml of an enzyme solution were mixed and reacted at 37° C. for 4 hours. Insoluble dextran yielded in the reaction solution was determined in the same manner as in Text Example 1.

TABLE 2

| Sugar Content in the Reaction Solution | Amount of Dextran Yielded in the Reaction Solution ($\gamma$) |
|---|---|
| Sucrose 10 mg | 740 (100) |
| Sucrose 10 mg + $GF_2$ 30 mg | 300 (40) |
| Sucrose 10 mg + $GF_3$ 30 mg | 350 (47) |

Additionally, numbers in the parentheses in Table 2 indicate indexes of the amounts of insoluble dextran, taking that yielded from sucrose as 100.

TEST EXAMPLE 3

Sweeteners having the following compositions were prepared by reacting sucrose in the presence of fructosyl transferase under various conditions.

TABLE 3

| No. | Fructose | Glucose | Sucrose | $GF_2$ | $GF_3$ | $GF_4$ | $GF_5$ | Ratio* |
|---|---|---|---|---|---|---|---|---|
| 1 | — | 5.9 | 81.9 | 12.2 | — | — | — | 15.0 |
| 2 | — | 13.7 | 58.5 | 27.8 | — | — | — | 47.5 |
| 3 | — | 17.4 | 41.8 | 35.7 | 5.0 | — | — | 97.0 |
| 4 | — | 23.5 | 23.9 | 41.2 | 11.4 | — | — | 220 |
| 5 | — | 28.4 | 14.9 | 39.2 | 17.4 | — | — | 380 |
| 6 | 0.8 | 31.5 | 11.0 | 26.4 | 25.1 | 5.0 | — | 514 |
| 7 | 0.9 | 31.6 | 10.0 | 23.5 | 24.1 | 7.0 | 2.9 | 575 |

$$* \frac{GF_2 + GF_3 + GF_4 + GF_5 (\%)}{\text{free sucrose}(\%)} \times 100$$

The amounts of insoluble dextrin yielded from the above-described transfer sugar compositions were measured in the same manner as in Test Example 1 to obtain the results indicated in Table 4.

TABLE 4

| Sample | Dextrin Yielded in the Reaction Solution (%) |
|---|---|
| Sucrose | 490 (100)* |
| Transfer Sugar No. 1 | 436 (89) |
| Transfer Sugar No. 2 | 298 (61) |
| Transfer Sugar No. 3 | 289 (59) |
| Transfer Sugar No. 4 | 201 (41) |
| Transfer Sugar No. 5 | 142 (29) |
| Transfer Sugar No. 6 | 44 (9) |
| Transfer Sugar No. 7 | 40 (8) |

*Numbers in the parentheses indicate indexes of the amounts of insoluble dextran, taking that from sucrose of 100

TEST EXAMPLE 4

*Streptococcus mutans* Serotype C was anaerobically cultivated using a medium containing 0.27% maltose, 0.01% L-cysteine hydrochloride, 0.1% sodium L-glutamate, 0.2% $NH_4H_2PO_4$, 0.02% $MgSO_4 \cdot 7H_2O$, 0.001% NaCl, 0.01% $MnSO_4$, and 0.01% $FeSO_4 \cdot 7H_2O$. Then, cells of the microorganism were collected by centrifugation, then dispersed in a 0.05M phosphate buffer in a concentration of 10 mg/ml. 0.9 ml of a 0.2M phosphate buffer, 0.14 ml of 22.5 mM $MgCl_2$, 0.2 ml of a 1.7% sugar solution, and 0.5 ml of the cell dispersion were mixed and shaked at 37° C. for 30 minutes to react. Then, the mixture was boiled for 15 minutes to discontinue the reaction and, after removal of the cells by centrifugation, lactic acid in the supernatant liquid was determined according to an enzymatic method.

TABLE 5

| Substrate | Lactic Acid, μmol/Reaction Solution | Production Ratio |
|---|---|---|
| Sucrose | 16.8 | 100 |
| $GF_2$ | 8.0 | 48 |
| $GF_3$ | 0.1 | 0 |
| Composition-1*[1] | 12.6 | 75 |
| Composition-2*[2] | 3.7 | 22 |

*[1]Composition-1: (sugar composition obtained by reacting sucrose in the presence of fructosyl transferase)
Glucose 37%
Fructose 2%
Sucrose 10%
$GF_2$ 22%
$GF_3$ 23%
$GF_4$ 6%

*[2]Composition-2: (composition obtained by catalytic reduction)
Sorbitol 38%
Mannitol 1%
Sucrose 10%
$GF_2$ 22%
$GF_3$ 23%
$GF_4$ 6%

Further, the main ingredients of the sweetener according to the present invention, i.e., $GF_2$, $GF_3$ and $GF_4$, are not susceptible to decomposition due to a disaccharide decomposing enzyme of rabbit intestine so that an increase in blood sugar level is greatly suppressed when compared with cases of using sucrose or glucose. This means that the sweetener composition of the present invention is a low-calorific sweetener.

These facts are demonstrated by Text Examples 5 and 6. In tests, as $GF_2$, $GF_3$ and $GF_4$, O-$\beta$-D-fructofuranosyl-(2→1)-O-$\beta$-D-fructofranosyl-(2→1)-$\alpha$-D-glucopyranoside (hereinafter referred to as 1-kestose), O-$\beta$-D-fructofuranosyl-(2→[1-O-$\beta$-D-fructofuranosyl-2]$_2$→1)-$\alpha$-D-glucopyranoside (hereinafter referred to as nystose), and O-$\beta$-D-fructofuranosyl-(2→[1-O-$\beta$-D-fructofuranosyl-2]$_3$→1)-$\alpha$-D-glucopyranoside (hereinafter referred to as 1F-fructofuranosyl-nystose), respectively.

TEST EXAMPLE 5

Intestinal disaccharide decomposing enzyme was prepared from the intestinal mucous membrane of a rabbit (body weight: 3 kg) according to the method of Y. Takesue (*Journal of Biochemistry*, Vol. 65, page 545 (1969)). The crude enzyme system showed 280 U/ml of sucrose activity, 540 U/ml of maltose activity and 8 U/ml of trehalase.

A mixture of 1.0 ml of a 5% substrate, 1.0 ml of a 0.25M phosphate buffer solution (pH 6.5) and 0.5 ml of the above prepared crude enzyme system was allowed to react at 37° C. for 24 hours. The resulting reaction mixture was subjected to high pressure liquid chromatography using a column of μ Bondapack CH (a registered trademark manufactured by Waters Ldt.) and acetonitrile-water (75:25) as an eluent to obtain a rate of decomposition. The results obtained are shown in Table 6. The rate of decomposition was calculated according to the following formula:

Rate of decomposition (%) = 100 − wt % of unreacted substrate based on total solid weight of the reaction mixture after 24 hrs' reaction

TABLE 6

Decomposition by Rabbit Intestinal Disaccharide Decomposing Enzyme

| Substrate | Rate of Decompositon |
|---|---|
| Sucrose | 100 |
| Maltose | 100 |
| 1-Kestose | 0 |
| Nystose | 0 |
| 1F-Fructofuranosyl-nystose | 0 |

As is shown in Table 6 above, 1-kestose, nystose and 1F-fructofuransoyl-nystose are not at all decomposed by the rabbit intestinal disaccharide decomposing enzyme.

TEST EXAMPLE 6

Wistar male rats (body weight: 170 g; 30 rats per group) were fasted for 17 hours. Each of the indicated saccharides was orally administered to the rats at a dose of 3 g/kg. After 30, 60, 90, 120 or 180 minutes from the administration, the blood was taken from 6 rats in each group, and the glucose level in blood was determined by a glucose oxidase method. The results obtained are shown in Table 7.

TABLE 7

Changes in Blood Sugar Level in Fasted Rats

| | 30 min. | 60 min. | 90 min. | 120 min. | 180 min. |
|---|---|---|---|---|---|
| Control (no admin.) | 100 | 100 | 100 | 100 | 100 |
| Sucrose | 287 | 254 | 221 | 163 | 177 |
| Glucose | 341 | 286 | 185 | 163 | 163 |
| Fructose | 236 | 252 | 246 | 232 | 183 |
| 1-Kestose | 139 | 122 | 121 | 123 | 123 |
| Nystose | 123 | 109 | 106 | 108 | 119 |
| 1F-Fructofuranosyl-nystose | 120 | 109 | 104 | 110 | 109 |

The values given in Table 7 above were represented as compared with the blood surgar level (mg/dl) of the control group which was taken as 100. The blood sugar levels of the control group after 30, 60, 90, 120 and 180 minutes were 61±4.3, 65±5.0, 67±2.3, 73±7.0 and 64±3.7, respectively.

As can be seen from Table 7, no increase in blood sugar level was observed in 1-kestose, nystose and 1F-fructofuranosyl-nystose groups. This indicates that the fructooligosaccharides of the present invention are not absorbed into bodies and, therefore, do not furnish substantial calory.

EXAMPLE 1

10 ml portions of BS medium containing 5.0% sucrose, 1.0% peptone, 0.7% meat extract, and 0.3% NaCl were respectively poured into two test tubes and, after sterilizing at 120° C. for 30 minutes, each of the media was inoculated with a platinum wire loop of *Aspergillus niger* ACE-2-1, ATCC 20611, and cultivation was conducted at 28° C. for 24 hours.

10 ml portions of the resulting culture solutions were respectively added to two Erlenmeyer flasks retaining 200 ml of BS medium (sterilized at 120° C. for 30 minutes), and shaking culture was conducted at 28° C. for 24 hours to conduct precultivation.

20 l of BS medium was charged in a 30-l jar fermentor and, after sterilizing at 120° C. for 30 minutes, cooled and inoculated with 400 ml of the aforesaid culture solution. Cultivation was conducted at 300 rpm at 28° C. for 72 hours. After completion of the cultivation, cells were removed by filtration to obtain 20 l of a culture filtrate. 20 l of this culture filtrate was concentrated and purified by ultrafiltration to obtain 2 l of an enzyme solution having an enzyme activity of 240 units/ml.

6.7 l of water was added to 10 kg of sucrose to dissolve and, after adjusting the pH to 5.0, the enzyme was added thereto in an amount of 48 units per g of sucrose, and the transfer reaction was conducted at 50° C. for 48 hours. After completion of the transfer reaction, the reaction mixture was heated to 100° C. for 15 minutes to deactivate the enzyme followed by adding activated carbon in a proportion of 0.5% based on solids to decolorize. After removal of the activated carbon, the solution was treated with ion-exchange resins of Amberlite IR-120B and Amberlite IRA-411, and concentrated to 75% w/w to obtain 12 kg of a low-cariogenic sweetener.

The thus-obtained sweetener had a sugar composition of: 26% glucose; 2% fructose; 18% sucrose; 40% $GF_2$; and 14% $GF_3$.

EXAMPLE 2

*Fusarium lini* IAM 5008 was cultivated in the same manner as described in Example 1 to obtain 20 l of a culture solution. This solution was concentrated and purified by ultrafiltration to obtain 2 l of an enzyme solution having an enzyme activity of 200 units/ml.

7 l of water was added to 3 kg of sucrose and, after adjusting pH to 6.0, the enzyme was added thereto in an amount of 16 units per g of sucrose followed by conducting the transfer reaction at 50° C. for 24 hours. After completion of the reaction, the solution was heated to 100° C. for 15 minutes to deactivate the enzyme, and activated carbon was added thereto in an amount of 0.5% based on solids to decolorize. Then, the solution was desalted with an ion-exchange resin, and concentrated to 75% w/w to obtain 3.7 kg of a low-cariogenic sweetener.

The thus-obtained sweetener had a sugar composition of: 38.2% glucose; 7.8% fructose; 17.2% sucrose; 25.4% $GF_2$; and 11.4% $GF_3$.

EXAMPLE 3

*Gloeosporium kaki* IAM 5011 was cultivated in the same manner as described in Example 1 to obtain 20 l of a filtrate. This filtrate was concentrated and purified by ultrafiltration to obtain 1.5 l of an enzyme solution having an enzyme activity of 200 units/ml.

7 l of water was added to 3 kg of sucrose to dissolve and, after adjusting pH to 6.0, the enzyme was added thereto in an amount of 20 units per g of sucrose followed by conducting the transfer reaction at 50° C. for 24 hours. After completion of the reaction, the solution was decolorized and desalted in the same manner as in Example 1, and concentrated to 75% w/w to obtain 3.8 kg of a low-cariogenic sweetener.

The thus-obtained sweetener had a sugar composition of: 25% glucose; 9% fructose; 36% sucrose; 24% $GF_2$; and 6% $GF_3$.

Examples of applying the sweetener to various foods and drinks will be described below.

EXAMPLE 4

Preparation of hard candy:

A low-cariogenic sweetener having a sugar composition of 37% glucose, 2% fructose, 10% sucrose, 22% $GF_2$, 23% $GF_3$ and 6% $GF_4$ (water content: 25 % by weight) was vacuum-concentrated to a final water content of about 8 to 10% by weight and, after cooling to about 80° C., a flavor and an edible dye were added thereto followed by casting and cooling to room temperature to obtain hard candy. This candy did not form crystals of sugar as with candy produced by using sugar, and was of low cariogenicity.

EXAMPLE 5

Preparation of orange marmalade:

200 g of orange flesh was added to 90 g of orange peel that had been dipped overnight in a 3% sodium chloride aqueous solution to remove bitterness, washed with water to remove the salt, and boiled for about 20 minutes. After adding thereto 370 ml of water, the mixture was boiled down for about 30 minutes while adding thereto 320 g of the low-cariogenic sweetener having the same sugar composition as Example 4 (water content: 25% w/w). The resulting orange marmalade had a sugar content of 65% w/w. This provided a refreshing acid taste of orange and was delicious.

EXAMPLE 6

Preparation of sweet paste of steamed beans (also referred to as "neri-yokan"):

12 g of agar-agar was dipped in water for 3 hours and ground after removing water. Then, 260 ml of water added thereto followed by heating to dissolve. 960 g of low-cariogenic sweetener having the same sugar composition as Example 4 (water content: 25% by weight) was added thereto, and filtered after agar-agar was completely dissolved. This agar-agar mixture was placed over a fire, and 500 g of raw bean paste was added thereto and kneaded and, after boiling down to obtain a sugar content of 70 to 71%, cast into a box and fixed to prepare sweet paste of steamed beans (neri-yokan). This had low cariogenicity.

EXAMPLE 7

Preparation of ice-cream:

10 parts of skim milk, 75.5 parts of water, 0.25 parts of a stabilizer, 0.25 parts of an emulsifying agent, 14 parts of low-cariogenic sweetener having the same sugar composition as Example 4, and a proper amount of flavor were used to prepare an ice-cream mix. After filitration, this was sterilized at 70° C. for 30 minutes, then cooled. After aging at 3° C. to 5° C. for 6 hours, the temperature was lowered while stirring to freeze. Thus, there was prepared ice-cream. Since the low-cariogenic sweetener had about the same freezing point depression, the resulting ice-cream had a good shape retention compared with the case of using sugar.

EXAMPLE 8

Preparation of biscuits:

Dough was prepared by using 1 kg of wheat flour, 100 g of corn starch, 333 g of the low-cariogenic sweetener having the same sugar composition as Example 4 (water content: 25% w/w), 125 g of margarine, 5 g of sodium chloride, 2.5 g of sodium carbonate, 8.8 g of ammonium carbonate, 6.3 g of soybean lecithin, 75 g of whole egg, 6.3 g of vanilla oil, and 267 g of water and, after expanding, molded and baked to prepare biscuits. The state of dough was the same as that in the case of using sugar, and the biscuits had a good volume and a good baked color as compared with the case of using sugar.

EXAMPLE 9

Preparation of a soft drink:

1.5 parts of citric acid and 970 parts of water were added to 133 parts of the low-cariogenic sweetener having the same sugar composition as Example 4 (water content: 25% w/w) to dissolve, and a colorant and a flavor were properly added thereto. Then, the mixture was subjected to carbonation to prepare a soft drink. This is a low-cariogenic soft drink, because it contains only the low-cariogenic sweetener.

EXAMPLE 10

Preparation of chewing gum:

75 parts of the low-cariogenic sweetener powder having the same sugar composition as Example 4 and 22 parts of chicle rubber were dissolved and mixed. Then, a flavor and menthol were added thereto followed by kneading. After subjecting it to rolling mill to roll into a definite thickness, the rolled product was cut and dried to prepare plate gum. This gum has low cariogenicity, because only the low-cariogenic sweetener was used.

EXAMPLE 11

Preparation of chocolate:

100 parts of bitter chocolate, 116 parts of low-cariogenic sweetener powder having the same sugar composition as Example 4, 25 parts of cacao butter, 90 parts of milk powder, and slight amounts of vanilla and lecithin were compounded to prepare chocolate in a conventional manner. This chocolate had a refined sweetness and gave the same test as that prepared by using sugar.

EXAMPLE 12

Preparation of preserved food boiled down in soy sauce (also referred to as "tsukudani):

1 liter of soy sauce and 900 g of the low-cariogenic sweetener having the same sugar composition as Example 4 were mixed and boiled down. Then, 800 g of short-necked clam and 50 g of ginger were added thereto and boiled for 40 to 60 minutes in a floating state to obtain preserved short-necked clam boiled down in soy sauce having a good color and a good taste.

EXAMPLE 13

Preparation of glazed chestnuts:

Epicarps of chestnuts were removed, followed by boiling the skinned chestnuts for 8 to 10 hours. Then, bitter skin was removed, and a 40% hot sugar solution of low-cariogenic sweetener having the same sugar composition as Example 4 was poured thereon. After allowing to stand for one day, a 45% sugar solution was poured thereon followed by allowing to stand for one day. Likewise, the concentration of the sugar solution was raised up to 70% to prepare glazed chestnuts. Since the osmotic pressure of the low-cariogenic sweetener was about the same as that of sugar, good products were obtained.

EXAMPLE 14

10 ml portions of BS medium containing 5.0% sucrose, 1.0% peptone, 0.7% meat extract, and 0.3% NaCl were respectively poured into two test tubes and, after sterilizing at 120° C. for 30 minutes, each of the media was inoculated with a platinum wire loop of *Aspergillus niger*, and cultivation was conducted at 28° C. for 24 hours.

10 ml portions of the resulting culture solution were respectively added to two Erlenmeyer flasks containing 200 ml of BS medium (sterilized at 120° C. for 30 minutes), and shaking culture was conducted at 28° C. for 24 hours to conduct pre-cultivation.

20 l of BS medium was charged in a 30-l jar fermentor and, after sterilizing at 120° C. for 30 minutes, cooled and inoculated with 400 ml of the aforesaid culture solution. Cultivation was conducted at 300 rpm at 28° C. for 72 hours. After completion of the cultivation, cells were removed by filtration to obtain 20 l of a culture filtrate. 20 l of this culture filtrate was concentrated and purified by ultrafiltration to obtain 2 l of an enzyme solution having an enzyme activity of 240 units/ml.

3.3 l of water was added to 5 kg of sucrose to dissolve and, after adjusting the pH to 6.0, the enzyme solution was added thereto in an amount of 60 units/g sucrose followed by the transfer reaction at 50° C. for 72 hours. After completion of the transfer reaction, the solution was heated at 100° C. for 15 minutes to deactivate the enzyme. Then, activated carbon was added thereto in an amount of 0.5% based on solids to decolorize. After removal of the activated carbon, the solution was treated with the ion-exchange resins of Amberlite IR-120 and Amberlite IRA-411, and concentrated to a concentration of 75% by weight to obtain 6 kg of a sweetener. This sweetener had a sugar composition of: 37% glucose; 2% fructose; 10% sucrose; 22% $GF_2$; 23% $GF_3$; and 6% $GF_4$.

700 ml of water was added to the above-stated sweetener composition, 15 ml of 10% $Na_2HPO_4$ was added thereto followed by adjusting the pH to 9.0 with 4% NaOH. 50 g of Raney nickel was added thereto, and reduction reaction was carried out at 80° to 90° C. for 50 minutes under stirring at a hydrogen pressure of 60 to 120 $kg/cm^2$. After completion of the reaction, the nickel catalyst was removed, and the solution was treated with the ion-exchange resins of Amberlite IR-120B and Amberlite IRA-411 followed by concentrating to 75% w/w to obtain 1 kg of a product. This sweetener had a sugar composition of: 38% sorbitol; 2% mannitol; 9% sucrose; 22% $GF_2$; 23% $GF_3$; and 6% $GF_4$.

EXAMPLE 15

10 ml of BS medium containing 0.5% sucrose, 1.0% pepton, 0.7% meat extract, and 0.3% NaCl were respectively poured into two test tubes and, after sterilizing at 120° C. for 30 minutes, each of the media was inoculated with a platinum wire loop of *Aureobasidium pullulans* var. melanigenum A-8 ATCC 20612, and cultivation was conducted at 28° C. for 24 hours.

10 ml of the resulting culture solutions were respectively added to two Erlenmeyer flasks retaining 300 ml of BS medium (sterilized at 120° C. for 30 minutes), and shaking culture was conducted at 28° C. for 24 hours to conduct pre-cultivation.

20 l of medium containing 10% sucrose, 1.0% pepton, 0.7% meat extract, 0.3% NaCl, 0.1% $CoCl_2.6H_2O$, was charged in a 30-l jar fermentor and after sterilization at 120° C. for 30 minutes, cooled and inoculated with 600 ml of the aforesaid culture solution. Cultivation was conducted at 240 rpm at 28° C. for 24 hours. After cultivation, cells were centrifuged to obtain 400 g of crude enzyme. This crude enzyme (cells obtained by centrifugation) had an enzyme activity of 12,000 units/g.

6.7 l of water was added to 10 kg of sucrose to dissolve and after adjusting the pH to 6.0, the enzyme was added thereto in an amount of 30 units per g of sucrose, and the transfer reaction was conducted at 60° C. for 48 hours. After completion of the transfer reaction, the reaction mixture was heated to 100° C. for 15 minutes to inactivate the enzyme followed by adding activated carbon in a portion of 0.5% based on solids to decolorize. After removal of the active carbon, the solution was treated with ion-exchange resins of Amberlite-120B and Amberlite IRA-411, and concentrated to 75% w/w to obtain 11 kg of a low-cariogenic sweetener.

The thus-obtained sweetener had a sugar composition of 0.8% fructose, 31.5% glucose, 11.0% sucrose, 24.6% $GF_2$, 25.1% $GF_3$, 7.0% $GF_4$.

While the invention has been described in detail and with reference to specific embodiments thereof, it will be apparent to one skilled in the art that various changes and modifications can be made therein without departing from the spirit and scope thereof.

What is claimed is:

1. A sweetened low-calorific and low-cariogenic food product comprising:
   (a) a low-calorific and low-cariogenic oligosaccharide sweetener; in physical admixture or in solution with
   (b) an unsweetened food consumable by humans, wherein said food product is sweetened due to the presence of said oligosaccharide, and wherein said oligosaccharide comprises a sucrose molecule having covalently bound thereto, 1 to 4 fructose molecules, and is represented by general formula (I):

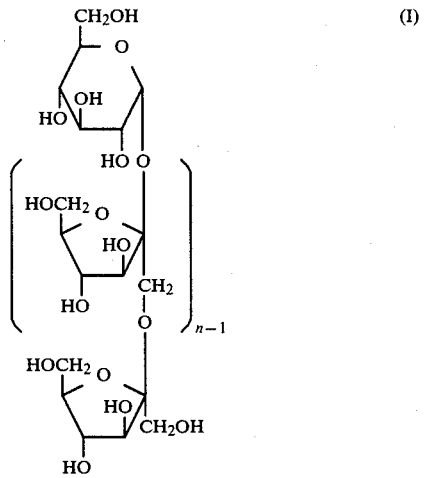

wherein $n=2-5$; or said oligosaccharide comprises mixtures of at least 2 of said oligosaccharides represented by formula (I).

2. The food product as claimed in claim 1, wherein said food product comprises, as an additional component, (c) free unbound sucrose, and wherein the ratio of the content by weight of the sum of said oligosaccharide to the content by weight of free unbound sucrose is at least 2.0/1.

* * * * *